United States Patent [19]

de la Caffiniere

[11] Patent Number: 5,192,281

[45] Date of Patent: Mar. 9, 1993

[54] UPPER LOCKING DEVICE FOR CENTROMEDULLARY PINS USED FOR OSTEOSYNTHESIS OF FRACTURES OF THE FEMUR, TIBIA, AND HUMERUS

[75] Inventor: Jean-Yves de la Caffiniere, Paris, France

[73] Assignee: Fixano SA, Bourg en Bresse, France

[21] Appl. No.: 818,892

[22] Filed: Jan. 10, 1992

[51] Int. Cl.⁵ .............................................. A61B 17/56
[52] U.S. Cl. ........................................ 606/59; 606/60
[58] Field of Search ...................... 606/59, 60, 61, 62, 606/65, 66, 67, 68, 72, 73, 95

[56] References Cited

U.S. PATENT DOCUMENTS

| | | | |
|---|---|---|---|
| 2,579,968 | 12/1951 | Rush | 606/62 |
| 2,658,508 | 11/1953 | Gibson | 606/62 |
| 4,055,172 | 10/1977 | Ender | 606/62 |
| 4,135,507 | 1/1979 | Harris | 606/62 |
| 4,169,470 | 10/1979 | Ender | 606/62 |
| 4,457,301 | 7/1984 | Walker | 606/62 |
| 4,467,793 | 8/1984 | Ender | 606/62 |
| 4,473,069 | 9/1984 | Kolmert | 606/64 |
| 4,474,177 | 10/1984 | Whiteside | 606/62 |
| 4,630,601 | 12/1986 | Harder | 606/62 |
| 4,653,487 | 3/1987 | Maale | 606/62 |
| 5,057,109 | 10/1991 | Olerud | 606/61 |

Primary Examiner—Robert A. Hafer
Assistant Examiner—Michael A. Brown
Attorney, Agent, or Firm—Oliff & Berridge

[57] ABSTRACT

A locking device has a metal locking part in which channels are provided to accommodate the upper ends of elongate pins. The lock preferably has a shape that is trapezoidal in longitudinal transverse section, has channels each having one blocked end to accommodate a pin, and is designed to be introduced into a recess of matching shape provided in the bone to be locked thereto. The ends of the pins, opposite the ends where the lock is located, are recurved to immobilize the pins relative to the bone both along their longitudinal axes and rotationally. The upper ends of pins are cut at the required length and introduced into the channels so that the upper blocked end of each of the channels of the lock opposes the upward and vertical forces transmitted by each of the pins.

10 Claims, 4 Drawing Sheets

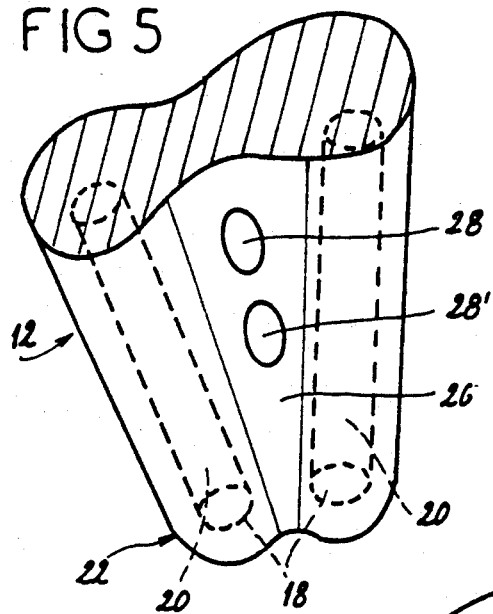
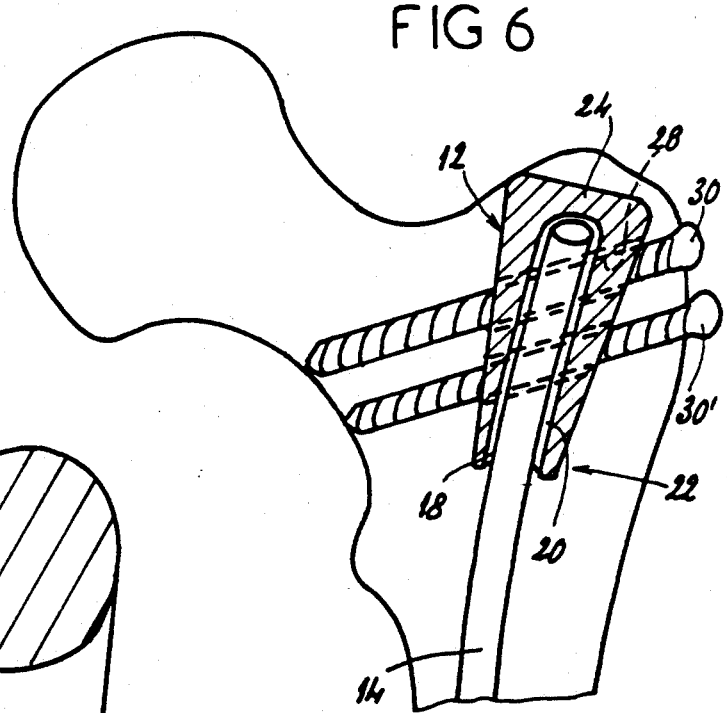
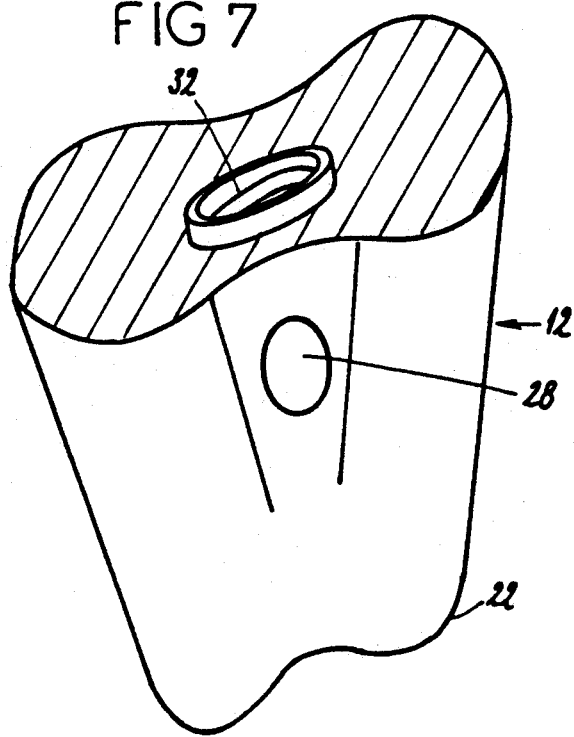

UPPER LOCKING DEVICE FOR CENTROMEDULLARY PINS USED FOR OSTEOSYNTHESIS OF FRACTURES OF THE FEMUR, TIBIA, AND HUMERUS

BACKGROUND OF THE INVENTION

The present invention relates to an upper locking device for centromedullary pins used for osteosynthesis of fractures of the femur, tibia, and humerus.

It is conventional to use pins for osteosynthesis of diaphyseal fractures, but this process is insufficient to control the rotary or vertical stresses acting on the fracture.

SUMMARY OF THE INVENTION

The present invention is designed to overcome this disadvantage by providing a device for ensuring full immobilization of the parts of the fractured member.

To this end, the device in question, which uses elongate pins and is of the type comprising a metal locking part in which channels are provided to accommodate the upper ends of the pins, is characterized by the fact that:

- the part called the "lock" preferably has a shape that is trapezoidal in lengthwise section, comprises channels to accommodate pins whose upper ends are blocked, and is designed to be introduced into a recess of matching shape provided in the bone and to be locked thereto;
- the ends of the pins located at the end opposite that where the lock is located are recurved to immobilize the pins relative to the bone both along their longitudinal axis and rotationally;
- the upper ends of the pins are cut at the required length and introduced into the channels of the lock so that the upper blocked end of each of the channels opposes the upward and vertical forces transmitted by each of the pins.

The locking of the pins to the parts of the fractured bone is thus perfectly assured, at one end, by their recurved shape which immobilizes them relative to the bone both along their longitudinal axis and rotationally, and at the other end, by the shape of the lock, its engagement in the bone, and its locking thereto. The lock ensures translational locking of the pins but can also, depending on the diameter of the channels receiving the ends of the pins, permit limited translation of the pins, so as to provide an assembly that has a certain degree of flexibility.

BRIEF DESCRIPTION OF THE DRAWINGS

In any event, the invention will be well understood from the following description with reference to the attached schematic diagrams showing as nonlimitative examples preferred embodiments of the device according to the invention.

FIGS. 2 to 6 are enlarged views at different angles and different stages of assembly, of the elements comprising the device; and FIGS. 7 to 9 are views of elements which supplement the device.

DESCRIPTION OF PREFERRED EMBODIMENTS

Figure 1:
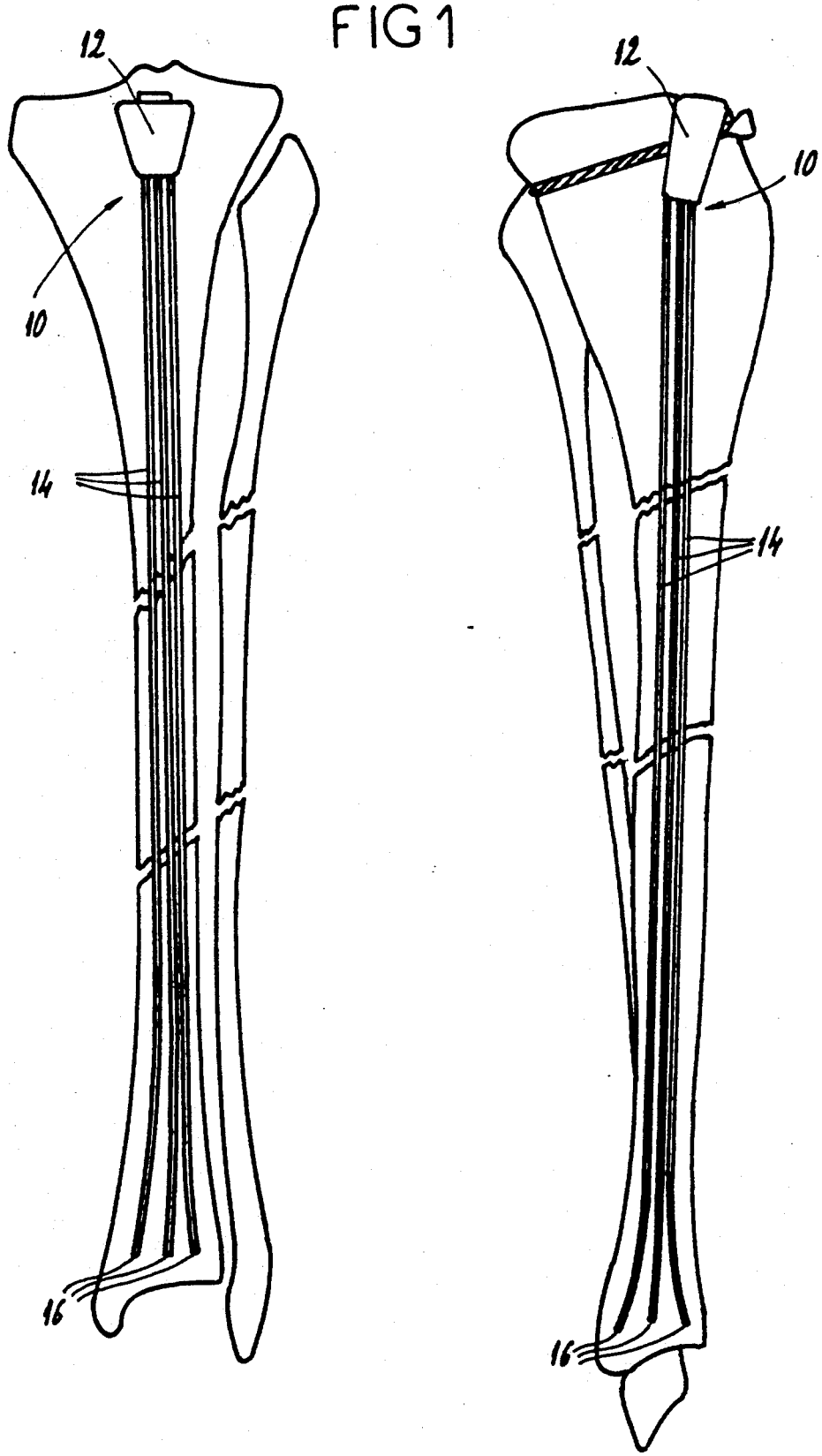
FIG. 1 shows the device according to the present invention from two different angles, mounted on a tibia.
Figure 2:
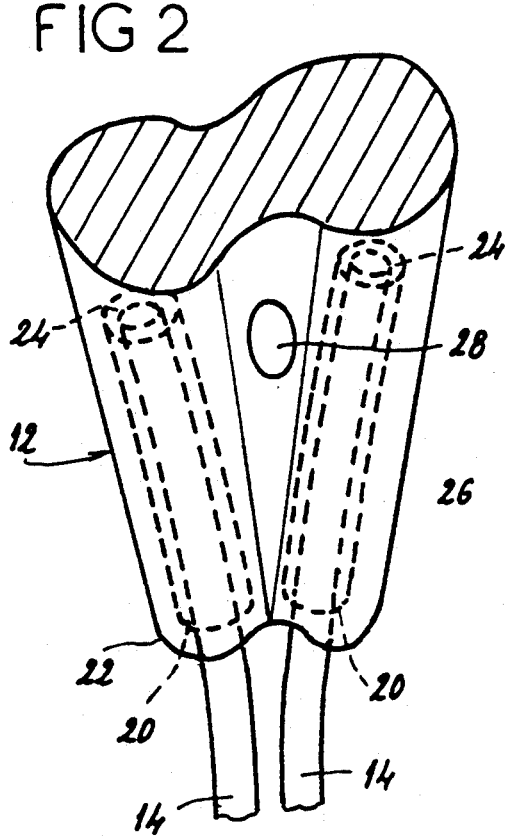
Figure 3:
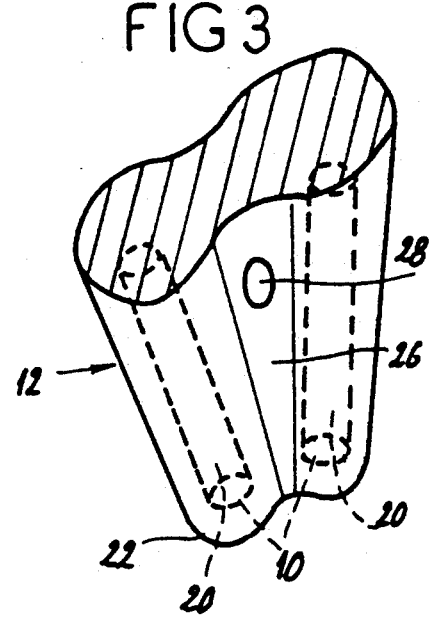

Referring to FIG. 1, it is evident that the device 10 according to the invention is composed of a metal lock 12 having a trapezoidal shape in lengthwise cross section, and pins 14 extending longitudinally from lock 12, designed to traverse a break in a bone. Pins 14 have ends 16, located opposite the ends where lock 12 is located, which are recurved and designed to abut the wall of the bone.

FIGS. 2 to 6 show the details of lock 12. Lock 12 is perforated along its major axis by two or four channels 20, depending on the model, extending from orifices 18 in the small base 22 of part 12 to terminal ends 24 which are closed. Internal channels 20, which receive the upper ends of pins 14, preferably diverge from one another, starting at orifices 18 and continuing to their ends 24.

Locks 12 have a thin median area 26 with one or two median holes or channels 28 whose axes are essentially perpendicular to channels 20 above.

Pins 14 are intended to be introduced into channels 20, while lock 12 is intended to be introduced into a recess provided in the bone having a shape which generally matches lock 12.

The upper blocked end 24 of each of channels 20 fully oppose the upward and vertical forces of each of the pins 14, with the pins 14 immobilized relative to the bone both along their longitudinal axes and rotationally. Limited translation of pins 14 relative to lock 12 is however possible, to ensure a flexible assembly.

Figure 4:
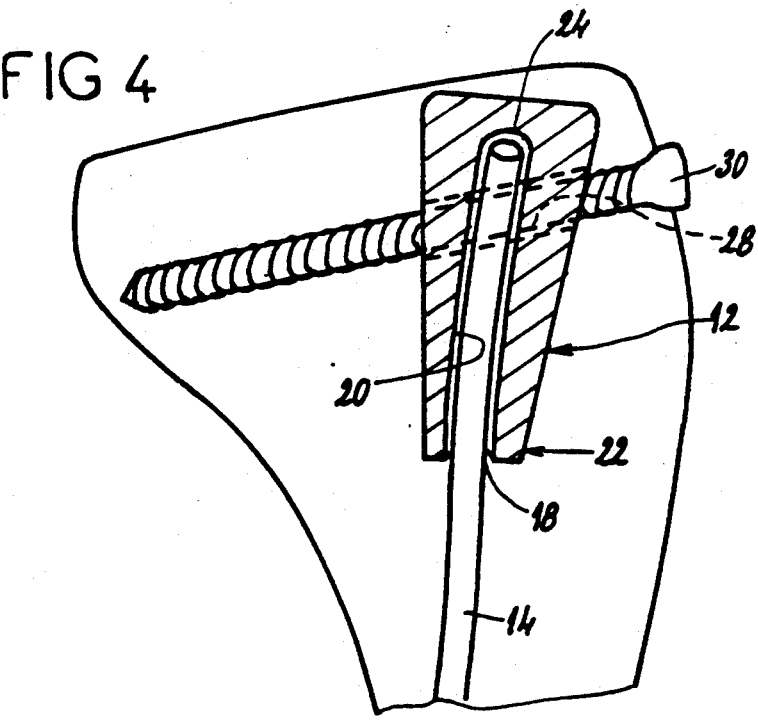

Lock 12 is locked to the bone by means of screws 30 introduced, using an aiming system, through the bone and through channels 28 in metal lock 12, as shown in FIG. 4.

In the lock used with a tibia shown in FIG. 4, as well as that used with a humerus, there is preferably only a single channel 28; and, locking is therefore provided by a single screw 30. Screw 30 is oriented about 15° downward relative to the horizontal plane as shown in FIG. 4.

For the lock used with a femur shown in FIG. 5, there are preferably two parallel channels 28 and 28' superimposed in the median area 26 of lock 12 and both oriented about 40° downward relative to the horizontal plane. These two channels 28 and 28' are sufficiently remote from one another to allow independent introduction of two locking screws 30 and 30', as shown in FIG. 6.

In addition, according to the present invention, there are three different models of locks of different sizes:

- the humeral part is the smallest and has only two vertical channels designed to receive two pins whose maximum size is about 3 mm;
- the tibial part is slightly larger, and can have two or four vertical channels to receive the ends of the pins whose maximum size is about 4 mm;
- the femoral part is the largest and has two or four vertical channels that can receive the ends of pins that can be about 5 mm in diameter.

Figure 8:
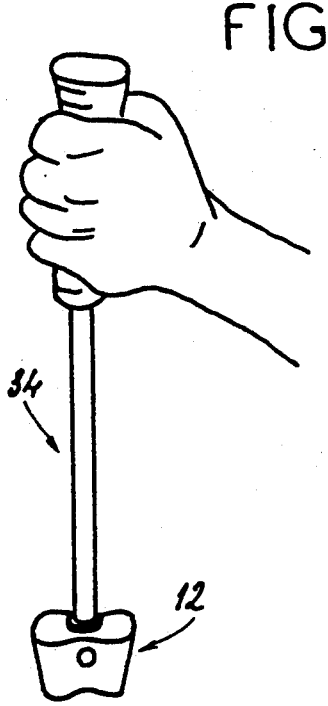

FIG. 7 shows a model of the lock equipped on its upper face with a screwing device 32 that permits introduction and screwing of the end of an auxiliary tool 34, shown in FIG. 8 for example, designed to support the lock while introducing the lock into the end of a bone for osteosynthesis or to hold the sight used to install the screws.

Figure 9:
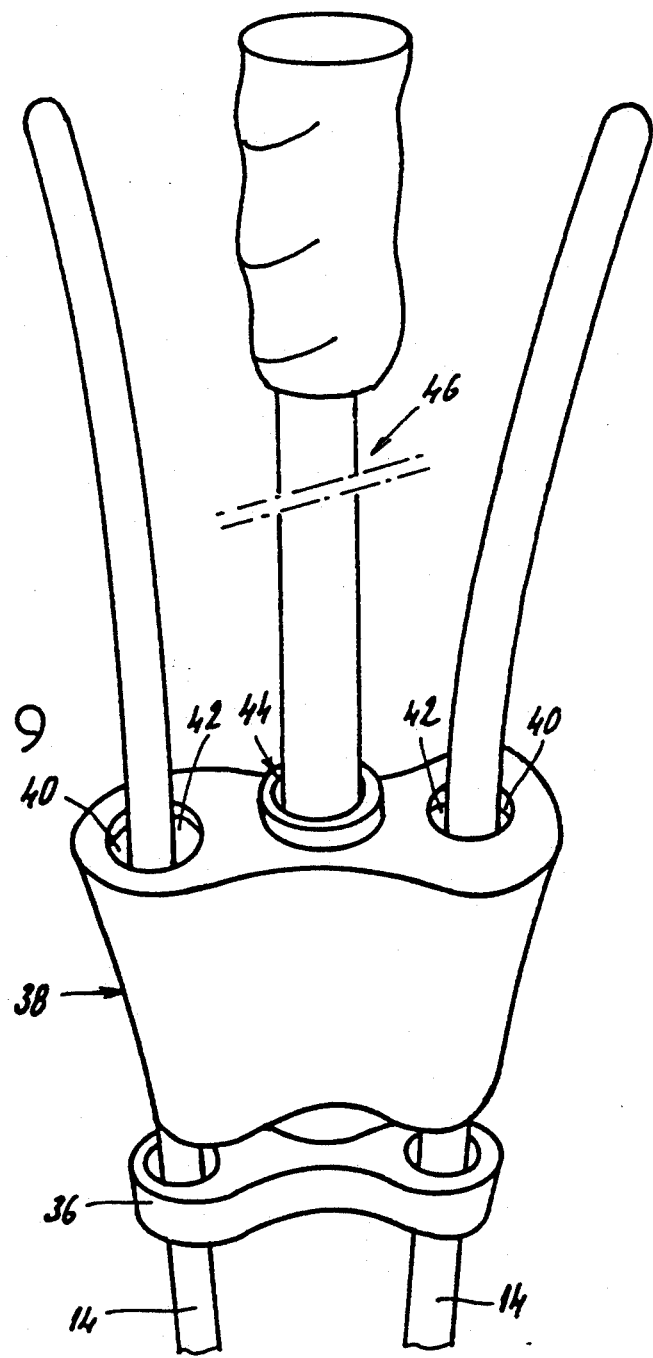

Among the auxiliary tools required for the installation of the lock is a pin separator 36 shown in FIG. 9 that is designed to spread the pins 14 automatically to prepare for introduction of the final lock. Pin separators 36 may have variable dimensions and may be provided with two, three, or four holes depending on the type of installation. Each separator 36 has a thickness sufficient to resist the stresses generated by spreading the pins. In operation, separator 36 is introduced downward after completing the installation of the central medullary pins and before the pin ends are cut.

To ensure the spreading of the ends of the pins and thus push the separator downward, a part called the "pilot device" 38 is used as shown in FIG. 9. Pilot device 38 is metal and resembles each of the basic models (femoral, tibial, and humeral). However, the pilot device is perforated all the way through by two or four holes 40 corresponding to the ends of the vertical channels 42 in the part. These channels 42, each having an inlet and exit hole, are designed to allow the installed pins 14 to pass through. The pilot device 38 is also provided on its upper face with a screwing device 44 for attaching pilot device 38 to a handle 46 fitted with a knob that permits easy manipulation. This handle 46 is removable and can be screwed onto each model of the test part.

Since three different models of the lock are provided, three pilot devices with two channels each and two other models with four channels each (femoral and tibial) are provided.

Thus, the pilot device can be used to introduce the separating elements and push them in place toward the medullary channel and prepare the bone for the final lock.

What is claimed is:

1. An upper locking device for centromedullary pins used for osteosynthesis of fractures of the femur, tibia, and humerus, comprising:
    a lock having a generally trapezoidal body having a lower end and an upper end, and a plurality of separate channels, each channel having one blocked end disposed toward the upper end of the body and one open end disposed at the lower end of the body, said body being designed to be introduced into a recess of matching shape provided in a bone to be locked thereto; and
    a plurality of elongate pins, each pin having first and second ends, the first end of each pin being adapted for axial introduction in one of the plurality of channels in the lock substantially in the direction of the longitudinal axis of each pin and the second end of each pin being located opposite the first end and being recurved to immobilize the pin relative to the bone both longitudinally and rotationally, the first end of each of the pins being divergent and being introducible into one of the channels so that the upper blocked end of each channel of the lock opposes the upward and vertical forces transmitted by the pin received in that channel.

2. A device according to claim 1, further comprising a pilot device with a shape resembling that of the lock and being perforated therethrough by a plurality of holes corresponding to the ends of the channels in the lock.

3. A device according to claim 2, wherein the pilot device is provided with a device for engagement with an auxiliary tool.

4. A device according to claim 1, further comprising a separator for separating the pins having a plurality of holes therethrough with a spacing generally equal to the spacing between the channels of the lock.

5. A device according to claim 1, wherein the channels diverge from each other between their open ends and their blocked ends.

6. A device according to claim 1, wherein the lock has at least one median channel generally perpendicular to the channels having one blocked end and one open end, said median channel comprising means for the introduction of screws which traverse the lock and the bone to secure the lock to the bone.

7. A device according to claim 6, designed for osteosynthesis of the tibia or humerus, wherein the lock has a single median channel oriented downward at an angle of about 15° to the horizontal.

8. A device according to claim 6, designed for the osteosynthesis of the femur, wherein the lock has two median channels that are generally parallel and oriented downward at an angle of about 40° to the horizontal.

9. A device according to claim 1, wherein the lock is provided with a device for engagement with an auxiliary tool.

10. A device according to claim 1, wherein the lock is made of metal.

* * * * *